United States Patent [19]

Kameny

[11] 4,062,365
[45] Dec. 13, 1977

[54] APPARATUS FOR GENERATING APPLIED ELECTRICAL STIMULI SIGNALS

[76] Inventor: Stanley L. Kameny, 13763 Raywood Drive, Los Angeles, Calif. 90049

[21] Appl. No.: 583,872

[22] Filed: June 5, 1975

[51] Int. Cl.² ............................................. A61N 1/36
[52] U.S. Cl. ................................................. 128/422
[58] Field of Search ...................... 128/421, 422, 423; 331/111, 113 R, 113 S; 307/271

[56] References Cited

U.S. PATENT DOCUMENTS

| | | | |
|---|---|---|---|
| 3,255,753 | 6/1966 | Wing | 128/421 |
| 3,718,132 | 2/1973 | Holt et al. | 128/427 |
| 3,897,789 | 8/1975 | Blanchard | 128/422 |
| 3,908,669 | 9/1975 | Man et al. | 128/422 |
| 3,911,930 | 10/1975 | Hagfors et al. | 128/421 |

Primary Examiner—William E. Kamm
Attorney, Agent, or Firm—Harvey S. Hertz

[57] ABSTRACT

An electrically operable stimulator and method for the control of pain or for other purposes through muscle and/or nerve stimulation by application of electrical pulses to the body of an animal, such as a human being. The stimulator generally comprises an internal power supply which may be rechargeable and which operates in conjunction with a pulse generator and an output amplifier. The pulse generator includes a unijunction transistor multivibrator and which is uniquely designed to achieve low current drain. Pulse interval and pulse width and pulse amplitude are controlled through separate and non-interacting controls. The output amplifier provides an output which is an excellent impedance match to the animal body for controlled stimulation. The output amplifier is uniquely designed to draw current only in proporton to the amount required, so that the entire apparatus is highly efficient.

8 Claims, 2 Drawing Figures

APPARATUS FOR GENERATING APPLIED ELECTRICAL STIMULI SIGNALS

BACKGROUND OF THE INVENTION

This invention relates in general to certain new and useful improvements in stimulators for application of electrical stimuli pulses to an animal body, and, more particularly, to electrically operable stimulators including a unique pulse generator and output amplifier.

There are several forms of electrical stimulators which haave been proposed for the relief of pain and similar purposes including body ailment healing and accordance of certain deleterious conditions which might otherwise arise. While the underlying pathogenesis which gives rise to these results is generally not understood fully, the clinical manifestation is certain and definite. For example, it has been found that application of electrical stimuli in proximity to an incision in thoracic surgery has been found to reduce the possibility of collapsed lungs.

Generally, it has been found that when using electrical stimulation from these electrical stimulators, with terminals applied to the body, that the output current introduced to the body has a substantial effect in reducing pain sensation and producing the other effects mentioned above. With respect to pain reduction, the exact phenomena in the reduction of pain also is not fully understood, although it has been determined that substantial pain reduction can be obtained through the application of such electrical pulses.

Those commercially available stimulators presently used include, in large measure, the now out-dated tube-type stimulators, primarily found in many physical therapy operations. There has been a recent introduction into the market place of these electrically operable stimulators constructed with solid-state circuitry. However, these stimulators suffer from a number of serious drawbacks in that they are difficult to use in that the controls of these mechanisms cause the various components of the circuit to interact in a rather complex way.

It is desirable to control the pulse width and the frequency and amplitude of signal outputs from these stimulators rather carefully, in order to achieve an optimum desired effect and to eliminate any unpleasant sensations for the patient. However, the prior art devices were not relatively effective in this regard since they were difficult to control, and consequently they have not been widely accepted.

The present invention obviates these and other problems in the provision of an electrical stimulator which includes a uniquely designed pulse generator and a uniquely designed output amplifier which permits precise control and generation of a desired output signal. The stimulator of the present invention also provides a greater range of applicability due to its ability to obtain close control and very reliable repeatability.

OBJECTS OF THE INVENTION

It is therefore the primary object of the present invention to provide an electrically operable stimulator and method for pain reduction which is capable of being easily and efficiently controlled for optimum desired electrical output signals.

It is another object of the present invention to provide an electrically operable stimulator of the type stated which can be manufactured to operate with a relatively small number of components and which can be constructed at a relatively low unit cost.

It is a further object of the present invention to provide an electrically operable stimulator of the type stated which is relatively simple in its operation and where relatively unskilled personnel can be easily trained in its operation.

It is yet another salient object of the present invention to provide an electrically operable stimulator of the type stated which is rugged in its construction and highly efficient in its operation.

With the above and other objects in view, my invention resides in the novel features of form, construction, arrangement and combination of parts presently described and pointed out in the claims.

SUMMARY OF THE INVENTION

The present invention relates to an electrically operable stimulator for the generation and application of electrical stimuli pulses to the body of an animal in order to create various desired physiological benefits including potential pain reduction. In general terms, the stimulator comprises a pulse generator comprised of a transistor based pulse generator which has been uniquely designed to provide a desired pulse form without suffering any current penalty. A pulse rate control means is operatively included in the generator for controlling the pulse rate of the output signal. A pulse width control means is also included to control pulse width. An amplifier output stage is also operatively connected to the pulse generator to produce pulses of the desired intensity. Furthermore, the amplifier output stage comprises a transformer means which is operatively connected to provide an output signal for application to the body of an animal.

In one aspect of the present invention, an off-on indicator light may form part of the pulse generator to provide indication of operation of the pulse generator. In addition, an indicator light may be provided and connected across the transformer means in order to provide indication of the storage level of the DC battery pack. In the same connection, a rechargeable source of stored electrical energy may form part of the stimulator and is operatively connected to the pulse generator.

The present invention also provides a method of providing electrical stimuli signals for application to an animal body in order to provide various physiological benefits including control of pain. This method will generally relate to the generating of a continuous series of electrical pulses. The method also includes the controlling of the pulse rate of these electrical pulses. In addition, the method includes a controlling of the pulse width of these electrical pulses independently of the pulse rate. Moreover, the amplitude of these pulses is controlled independently of the pulse rate and the pulse width to generate the desired output signal.

BRIEF DESCRIPTION OF THE DRAWINGS

Figure 1:
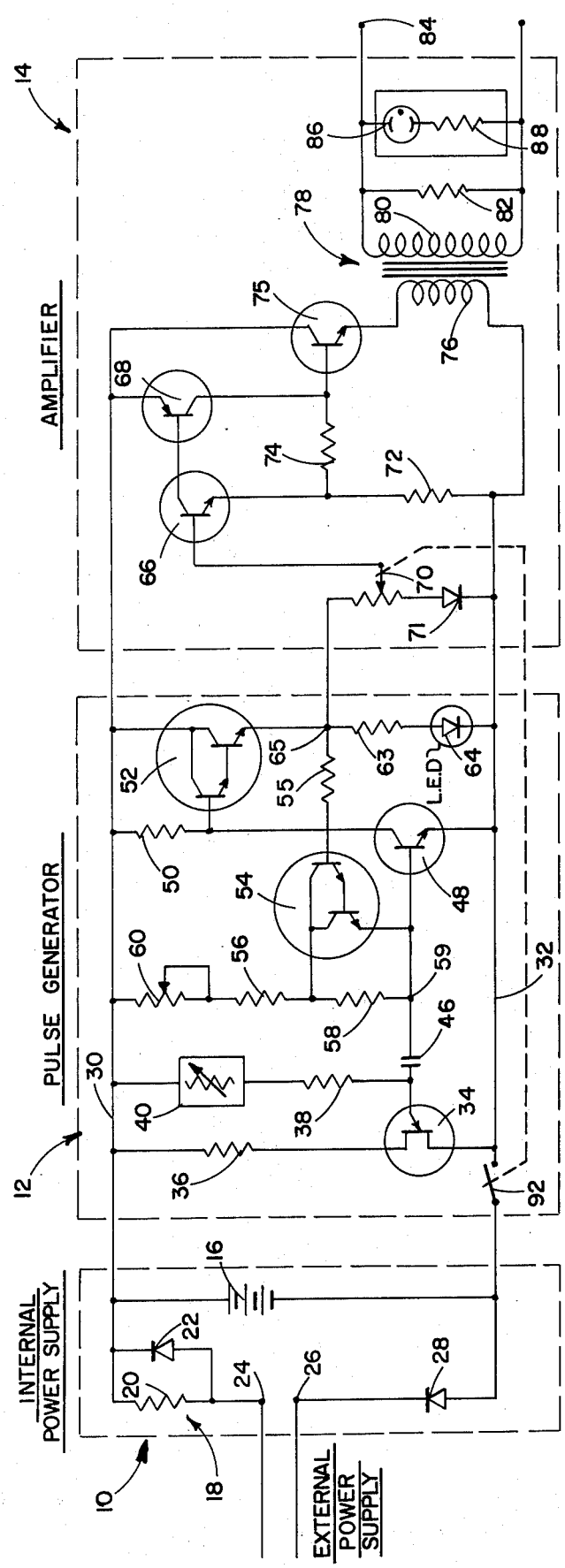
Figure 2:
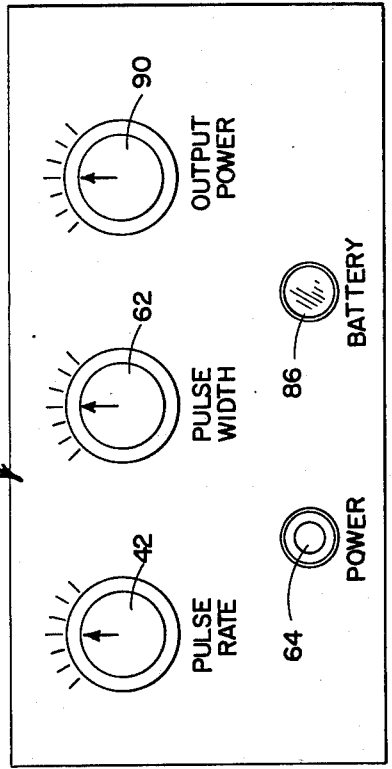

Having thus described my invention in general terms, reference will now be made to the accompanying drawings in which:

FIG. 1 is a schematic view of an electric circuit forming part of the stimulator of the present invention; and FIG. 2 is a front-elevational view of a control panel forming part of the stimulator of the present invention.

DETAILED DESCRIPTION

Referring now in more detail and by reference characters to the drawings which illustrate a preferred embodiment of the present invention, A designates an electrically operable stimulator which produces physiologically beneficial results including, for example, the potential elimination of various undesirable results arising after surgery and for pain reduction. The stimulator A may be used as a percutaneous stimulator or as a transcutaneous stimulator, although the invention is highly effective as a transcutaneous stimulator.

The stimulator A comprises an internal power supply 10, a pulse generator 12, and an output amplifier section 14, as illustrated in FIG. 1, and each of which is more fully described in detail hereinafter. These components would be suitably mounted in a conventional housing (not shown) and which would be provided with a control panel C, more fully illustrated in FIG. 2 of the drawings.

In general, the electrically operable stimulator is used in conjunction with a pair of electrodes which are suitably connected to a desired location of the body for introducing electrical signals thereto, and these signals are generally in the form of a train of electrical pulses. The terminals will be connected to a pair of outputs on the output amplifier section 14, as more fully described hereinafter. These terminals are essentially conventional in construction, and are therefore neither illustrated nor described in any further detail herein.

With respect to the present invention, the electrically operable stimulator has been described as being used for the effective muscle and/or nerve stimulation through application of electrical signals to the body of an animal. Generally, the animal will adopt the form of a human being, although it should be understood that the invention could be operable with any form of animal type having a central nervous system. Moreover, the electrical signals are analog signals which generally exist in the form of a series of pulses as indicated.

The internal power supply 10 generally comprises a rechargeable battery pack, as for example a conventional DC battery source, designated as 16. A recharging circuit 18 is connected across the terminals of the battery 16 and includes a load resistor 20 and a diode 22 connected in parallel to one input terminal 24. In like manner, the other input terminal 26 is provided with a rectifying diode 28. By definition, these input terminals 24 and 26 could be suitably connected to an external power supply (not shown) in order to provide a source of power for recharging the battery pack 16. In this respect, the battery operation and the recharging circuit are not absolutely essential to the present invention, except to allow greater ruggedness of construction.

The positive and negative output terminals of the battery 16 are connected to conductors 30 and 32 in the manner as illustrated in FIG. 1 of the drawings. In this case, it can be seen that the pulse generator 12 and the output amplifier 14 are connected across these conductors 30 and 32. The pulse generator 12 generally is constructed on the basis of a unijunction transistor multivibrator which has been modified substantially, at least through the provision of a high source impedance current matching amplifier and a current limiting switching transistor, in order to achieve a low current drain and low output impedance, for the pulse generator 12 at its output node 65 referred to negative conductor 32.

The pulse generator 12 comprises a pulse trigger 34 in the form of a unijunction transistor and which has the base-2 terminal thereof connected to the negative conductor 32 and the base-1 terminal thereof connected to the positive conductor 30 through a compensating resistor 36. The resistor 36 is designed to provide temperature compensation and also serves as a current limiting resistor for the unijunction transistor. The emitter of the unijunction transistor 34 is connected through a resistor 38 to a potentiometer 40 or other form of condensor charging control device, for control of current. In this respect, and by reference to FIG. 2, it can be observed that the potentiometer 40 is provided with a control knob 42 mounted on the front control panel C forming part of the stimulator of the present invention.

It should be understood that the term unijunction transistor as used herein will include the programmable unijunction transistor, and in which case the gate electrode (corresponding to the emitter electrode of the transistor 34) would be connected to the resistor 38. Moreover, the resistor 38 is merely auxiliary to the resistive potentiometer 40 and forms part of a resistive ladder therewith.

A capacitor 46 is also connected to the emitter of the unijunction transistor 34 and to an NPN transistor 48 which serves as a pulse forming transistor. The emitter of the transistor 48 is connected to the negative conductor 32 and the collector of the transistor 48 is connected through a resistor 50 to the positive conductor 30, in the manner as illustrated in FIG. 1.

The pulse generator 12 is also provided with a high current gain, high impedance amplifier 52 in the form of a pair of base-emitter connected NPN transistors, or so-called Darlington configuration, as shown in FIG. 1 of the drawings. It can be observed that the amplifier 52 has the base of one of its transistors connected to the collector of the pulse forming transistor 48 and the common collector terminal of the amplifier 52 connected to the positive conductor 30. The amplifier 52 effectively serves as an impedance changing amplifier and is designed to provide a low impedance output in a manner hereinafter described.

The pulse generator 12 also includes a current limiting resistor 58 and a shorting switch 54 (preferably composed of two transistors in the Darlington configuration) as connected in FIG. 1 of the drawings. In this case, one of the transistors in the switch 54 has a base which is driven by the emitter output of one of the transistors in the amplifier 52 through a coupling resistor 55. The switch 54 is connected to the base of the transistor 48 and the resistor 55 also is connected to the output of the amplifier 52 at output node 65.

The collector terminal of the Darlington configured transistors in the shorting switch 54 is connected through a resistor 56 to a pulse width control potentiometer 60, the latter also having one terminal connected to the positive conductor 30. The potentiometer 60 is operable by means of a pulse width control dial 62 mounted on the control panel C, as illustrated in FIG. 2 of the drawings. Again, the resistor 56 is auxiliary to the potentiometer 60 and forms part of a resistive ladder therewith.

The collector terminal of the shorting switch 54 is also connected to the current limiting resistor 58 which is, in turn, connected to the capacitor 46, the emitter terminal of shorting switch 54 and the base of the pulse forming transistor 48 at a junction 59, in the manner as illustrated in FIG. 1.

The output of the amplifier 52 is connected through a resistor 63 and a light emitting diode 64, the other terminal of which is connected to the negative conductor 32. The light emitting diode 64 is also mounted on the control panel C and is included to provide an indication of a "power-on" condition, when energized through the circuit of the present invention. It can be observed that the use of the resistor 63-diode 64 circuit is only optional and not necessary in the present invention.

By further reference to FIG. 1, it can be seen that the emitter output terminal of the amplifier 52 is connected to a common junction with the resistor 55 and the resistor 63 to form an output node 65. Thus, the amplifier 14 is effectively connected to this output node 65, as well as the positive and negative conductors 30 and 31, respectively.

In essence, the unijunction transistor 34, the pulse forming transistor 48 and the capacitor 46, along with the resistors 36 and 50, the combination resistance ladder comprised of resistors 38 and 40 and combination resistance ladder comprised of resistors 56 and 60, form a pulse generator. The resistor 36 serves as a compensating resistor in this pulse generator.

The high source impedance amplifier 52 permits a high value of load resistor 50 to be used in conjunction with the pulse-forming transistor 48, to reduce the collector current of transistor 48. This improves circuit efficiency, since the transistor 48 is active when the pulse generator 12 is in the "off" state only.

It can be observed that the switch 54 and the resistor 58, in combination, provide a unique current controlling switching means with respect to the circuit of the present invention in permitting generation of narrow pulses. Without the presence of these two components, if the potentiometer 60 were set to a low value, then a high current would flow through the base-emitter through the circuit of pulse-forming transistor 48 during the "off" state of the pulse generator, which would accomplish no useful work whatsoever. It can also be observed that a high current flow through the transistor 48 would otherwise exist inasmuch as the switch 54 is off when the capacitor 46 is charging; but when the transistor 48 is conducting, the resistor 58 keeps a low current through the transistor 48 since the switch 54 is cut off.

The cyclic operation of the pulse generator 12 is explained as follows. When the circuit is energized, a small amount of current will initially flow through the resistor 36 and the capacitor 46 will be charged through the potentiometer 40 and the resistor 38. Moreover, a circuit will be completed through the transistor 48 to the ground line 32.

As the emitter voltage in the transistor 34 increases toward a firing point, the voltage in the capacitor 46 will increase, and when the emitter voltage does reach the firing point, the unijunction transistor 34 is triggered to the "on" condition. The emitter voltage will then fall and the capacitor 46 will then discharge so that the voltage potential at the junction 59, namely the connection between the resistor 48 and the capacitor 46, falls. This will, in turn, cause the transistor 48 to switch to the off condition and cause a pulse to appear at the collector of the transistor 48. The amplifier 52 will then conduct, producing an output voltage at the output node 65.

The voltage at the output node will also be applied to the shorting switch 54 which effectively shorts out the resistor 58. Current will then flow through the resistor 56 and the potentiometer 60, discharging the capacitor 46 until the voltage on the base of the transistor 48 rises to a point where the transistor 48 again conducts. At this time, the emitter current to the unijunction transistor 34 drops, turning off the unijunction transistor so the emitter voltage at the amplifier 52 will drop, turning off the amplifier 52. The voltage at the output node 65 will then fall to essentially zero.

The transistor 54 will then cease to conduct and the resistor 58 is then switched into the circuit in series with the resistor 56 and the potentiometer 60, thereby limiting the current flow through the base to emitter of the transistor 48. The capacitor 46 will recharge through the potentiometer 40 and the resistor 38, and the cycle will again start over.

The operation of the pulse generator 12 has been described somewhat in connection with the description of the components of this circuit. However, the following describes the operation of this generator in greater detail. In this description, all voltages are given relative to the negative conductor 32.

When the pulse generator circuit is initially energized by closing a switch 92 (hereinafter described), or at the end of the discharge cycle of the capacitor 46 when the pulse generator has completed its pulse output, the capacitor 46 is uncharged, and the unijunction transistor 34 is in a low-conductance state in which almost no current flows through the unijunction transistor 34. The capacitor 46 then begins to charge, with the current flowing from the common positive conductor 30 through the resistors 40 and 38, the capacitor 46 and the base to emitter circuit of transistor 48 to the negative common conductor 32. Initially, both the left and right sides of the capacitor 46 are at the same voltage, which is the diode offset voltage of the transistor 48, typically approximately 0.5 volts. An additional current is supplied from the conductor 30 through the potentiometer 60, the resistor 56, and the resistor 58, and from base to emitter to transistor 48 to the negative conductor 30. This additional current, while small, is sufficient to cause the transistor 48 to allow a current to flow from conductor 30 through the load resistor 50, the collector to emitter circuit of the transistor 48 and to the conductor 32, so that the voltage at the input to the amplifier 52, which is the connection between the transistor 48, the resistor 50 and the amplifier 52, is below the conduction threshold for the amplifier 52. No current flows through the output emitter of the amplifier 52 so the voltage at the output node 65 is essentially zero, and the shorting switch 54 also has its input voltage below the threshold level and so no current flows through the shorting switch 54. These conditions regarding the transistor 48, the shorting switch 54 and the amplifier 52 persist unchanged throughout the charging cycle of the capacitor 46.

It is a property of the unijunction transistor 34 that some current flows in the circuit from the conductor 30 through the resistor 36, the upper base of the unijunction transistor 34, namely base-2, and thence to the lower base (base-1) of the unijunction transistor and to conductor 30. This current is greater when the unijunction transmitter fires than when the unijunction transistor is in the low conductance state. However, in the pulse generator described here, current through the resistor 36 is of no significance except that proper choice of the value of resistor 36 provides excellent temperature compensation for the operation of the pulse generator.

As the capacitor 46 charges, the voltage on the left side of the capacitor 46, and hence on the emitter of the unijunction transistor 34, rises until the emitter of the unijunction transistor 34 reaches a fixed, reproducible firing voltage, which is a predetermined portion of the voltage supplied by the conductor 30. At this time, which is dependent primarily upon the values of the capacitor 46 and the sum of resistors 38 and 40, the unijunction transistor 34 abruptly begins to conduct, and the voltage at the emitter of the unijunction transistor 34 and the left side of the capacitor 46 falls to a low diode offset value, typically about 0.5 volts. The voltage at the right side of the capacitor 46, and hence also the junction 59 and the base of the transistor 48, falls by the same amount, to a negative value. At this time, the transistor 48 ceases to conduct, the input voltage to the amplifier 52 rises to the voltage of the conductor 30, the amplifier 52 conducts, the voltage at the output terminal 65 rises to a fixed value, and current flows through the resistor 55 to the input of the shorting switch 54, which shorts the resistor 58, effectively connecting the resistor 56 to the junction 59. Current also flows from the output terminal 65 through the resistor 63 and the light-emitting diode 64, furnishing a visual indication that a pulse is being generated, and flows from its output terminal 65 to the amplifier section 14.

These conditions relative to the transistor 48, the amplifier 52, the shorting switch 54, and the connections to output terminal 65 remain constant for the duration of the capacitor discharge cycle, which is the time during which the pulse generator actively delivers its output pulse. The capacitor 46 is discharged by current flowing from conductor 30 through the potentiometer 60 and the resistor 56, the collector to emitter output current of the shorting switch 54, capacitor 46, and the emitter to lower base, i.e., base-1 of the unijunction transistor 34 to the conductor 32.

The capacitor continues to discharge until the voltage at the junction 59, and hence at the base of transistor 48, reaches the threshold value at which time the current at the junction 59 is diverted into the base-to-emitter circuit of the transistor 48, and the current flow to the emitter of unijunction transistor 34 drops abruptly. The unijunction transistor 34 returns to the original low conduction state, the amplifier 52 is turned off, the shorting switch 54 ceases to conduct, the voltage at the output terminal 65 falls to zero, and the charging cycle begins again.

In accordance with the above, it can be observed that the discharge time of the capacitor 46 is related to a function of the resistance set by the potentiometer 60 and is not at all related to the resistor 58. The resistor 58 is only effectively included in the circuit when the capacitor 46 is not discharging. In essence, when the capacitor 46 does discharge, the resistor 58 does not operate functionally in terms of controlling charging and discharging with respect to the capacitor 46.

In the circuit of the present invention, the amount of current consumed during the off time is very low and is therefore almost independent of setting. The resistors 50 and 58 are active during the off time, and both are of a high impedance. For example, the resistor 58 may have an impedance of 40,000 ohms, and the resistor 50 may have an impedance of 50,000 ohms or more.

In accordance with this construction, it can be observed that the pulse generator provides a stable frequency which is essentially independent of on time controls, and only dependent on off time control. Moreover, the circuit is not dependent on the amount of power drawn by the amplifier section hereinafter described; and thus is independent of output control. It should be understood, nevertheless, that the invention is still highly effective and could operate by merely using fixed resistances in place of the potentiometers 60 and 40. Furthermore, the circuit consumes a negligible amount of power. By manipulating the potentiometer 40, it is possible to control the pulse rate of the output signal. In like manner, by controlling potentiometer 60, it is possible to control the pulse width.

The amplifier output section is also more fully illustrated in FIG. 1 of the drawings and comprises an NPN transistor 66 having its collector connected to the base of a PNP transistor 68. The base of the transistor 66 is connected through the movable arm of a potentiometer 70 which, in turn, receives the output of the pulse generator 12 from the node 65. The emitter of the transistor 66 is connected through a resistor 72 to the negative conductor 32 and also through a resistor 74 to the collector of the transistor 68 and also to the base of the final power output NPN transistor 75. The collector of the transistor 75, as well as the emitter of the transistor 68, are connected to the positive conductor 30, in the manner as illustrated in FIG. 1 of the drawings.

The transistor 66 and the transistor 68 serve as a high source impedance amplifier section, and provide voltage and current amplification with feedback. Moreover, these two transistors serve as a voltage amplifier featuring high input impedance and low output impedance. The transistor 75 makes the output impedance very low.

The lower terminal of the resistive element forming part of the potentiometer 70 is connected to the negative conductor 32 through a diode 71 to bias the amplifier section 14 input in order to provide linearity at the potentiometer 70. In essence, this diode 71 could actually be a resistor since it is designed to offset the base-to-emitter voltage in the transistor 66.

The emitter of the transistor 75 is further connected through the primary coil 76 of a transformer 78 and to the negative conductor 32. The primary coil 76 of the transformer 78 generates a current in a secondary coil 80 of this transformer 78 which has a damping resistor 82 connected thereacross and provides a pair of output terminals 84. The electrodes mentioned above, which are designed for contact with the animal body, are connected to these output terminals 84.

A neon bulb with a series connected current limiting resistor 88 is connected across the terminals 84 to provide indication of the condition of the battery 16 when no load is connected to the output terminals 84. As the battery condition thus deteriorates, a greater voltage position on the potentiometer 70 will be required to energize the bulb 86. Thus, if the battery 16 has been seriously discharged, the neon bulb 86 will not be energized to emit light. It should also be observed that the neon bulb 86 is also mounted on the control panel C, in the manner as illustrated in FIG. 2 of the drawings.

The potentiometer 70 also provides for control of the output current and will therefore be provided with a control knob 90 which is suitably mounted on the control panel C. The exact arrangement for connecting the various control knobs 42, 62 and 90 to their associated components is conventional, and therefore has neither been illustrated nor described in any further detail herein. In this respect, it should be observed that the potentiometer 70 is also physically connected to a main power switch 92 which is located in the negative conductor 32 and serves to energize or de-energize the entire stimulator A. By physically connecting the switch 92 to the potentiometer 70, it is possible to obviate the problems which could otherwise result from surges when the switch 92 is initially turned to the "on" condition if the electrodes connected to the output terminals 84 were attached to the body of a patient. The switch 92 can also be suitably mounted on the control panel C. In actual practice, the switch 92 would by physically incorporated in the potentiometer and would be operable by the shaft of the potentiometer 70.

By using feedback to the arrangement of the transistors 66 and 68, the pulse voltage input at the coil 76 is proportional to the voltage established by the potentiometer 70. The feedback at the transistor 66 is based on the current on the collector being about eighty times greater than the current at the base thereof.

The resistors 74 and 72 act as a voltage divider such that when voltage at the collector of the transistor 68 is greater than that at the emitter of the transistor 66, current flows through the resistors 74 and 72 which will maintain current input to the transistor 66 at a very low level, thus producing a high impedance at the base of the transistor 66.

The amplifier section 14 is actually a two-stage amplifier with the transistors 66 and 68 constituting the first stage and the transistor 75 constituting the second stage. The stage comprised of the transistors 66 and 68 actually functions as a current and voltage amplifier with a feedback such that the gain thereof is almost completely dependent on the values of the resistors 72 and 74. The transistor 75 receives an output from the collector of the transistor 68 and the current passing through the resistor 74 less that amount used in the feedback path through the resistor 74. This emitter follower configuration employing transistor 75 provides a high current amplification to match the low input impedance of the coil 76.

One of the unique aspects of the amplifier output section 14, or so-called "amplifier output stage", is that this amplifier output stage 14 only draws current in proportion to the setting of the output power knob, thereby lending to a highly efficient operation. Moreover, by placing the output control potentiometer where it is in close relation to the transformer 78 and by utilizing the resistor 82, the transformer 78 is well damped over its entire range. Furthermore, this amplifier is designed so that it is an excellent impedance match for the human body as well as most warm-blooded animal bodies having a central nervous system to provide transcutaneous stimulation. It can be observed that if the impedance was too high, any movement of the electrode would create a burning sensation on the animal.

The transistors 66 and 68 actually constitute a voltage-current amplifier with feedback to raise the maximum voltage available to the base of the transistor 75 close to the available voltage of the power supply. The voltage at the output of the pulse generator 12 is reduced by over a one-volt level due partially to the characteristics of the transistors of the amplifier 52. The ratio of the values of the resistor 74 plus the value of the resistor 72 as divided by the value of the resistor 72 is designed to restore any voltage loss.

In accordance with the above, it can be observed that the pulse shape at the output terminals 84 is independent of all three settings of the generator A. In addition, all three pulse control functions are independent of each other. The output waveform has no D.C. component and, therefore, any electrophoretic effects are minimized. Since the amplifier section has no effect on the pulse generator, it is possible to provide more than one parallel amplifier section in cases where more than two electrodes are desired to be used. These additional amplifier sections would be connected to conductors 30 and 32, the pulse generator output at the node 65 and could, in addition, contain on-off switches in parallel with the switch 92.

Thus there has been illustrated and described a novel electrically operable stimulator for generating and applying electrical stimuli signals to an animal body to accomplish various beneficial physiological results including the control of pain and which therefore fulfills all of the objects and advantages sought therefor. It should be understood that many changes, modifications and other uses and application may be made by those skilled in the art based on the specification and the accompanying drawings. Therefore, any and all such changes, modifications and other uses and applications which do not depart from the nature and spirit of the invention are deemed to be covered by the invention which is limited only by the following claims.

Having thus described my invention, what I desire to claim and secure by Letters Patent is:

1. An electrically operable stimulator for generation and application of electrical stimuli signals to the body of an animal for control of physiological body conditions, said stimulator comprising:
   a. a pulse generator comprised of:
      1. unijunction transistor triggering means for energizing said pulse generator when said triggering means is switched from an off condition to an on condition,
      2. pulse generating transistorized means,
      3. capacitor means interposed in series relationship to said transistorized means and said triggering means,
      4. a high gain and high impedance control amplifier in said pulse generator for deriving and presenting an output signal,
      5. a shorting switch operatively connected to and operable by said control amplifier, and
      6. a current limiting resistor connected in relation to said shorting switch and to control current flow relative to charge and discharge times of said capacitor,
   b. amplifier means operatively connected to said control amplifier means of said pulse generator and comprising:
      1. a first amplifier section and a second amplifier section,
      2. an output level control means operatively connected to said first and second amplifier sections,
      3. transforming means operatively connected to said first and second amplifier sections to provide an output signal for application to the body of an animal.

2. The electrically operable stimulator of claim 1 further characterized in that a pulse rate control means is operatively connected to said transistorized means.

3. The electrically operable stimulator of claim 1 further characterized in that said stimulator comprises a pulse width control means to vary the pulse width of the signal generated in said pulse generator.

4. The electrically operable stimulator of claim 1 further characterized in that said output level control means comprises a potentiometer at the amplifier means input to control the size of the output signal.

5. The electrically operable stimulator of claim 1 further characterized in that said first amplifier section of said amplifier means comprises a first stage amplifier with high input impedance, high current gain, some voltage gain and a low output impedance, and a second stage amplifier with moderately high input impedance, high current gain, and very low output impedance.

6. The electrically operable stimulator of claim 5 further characterized in that said second amplifier section of said amplifier means comprises a third amplifier transistor interposed between said second amplifier transistor and said transforming means.

7. The electrically operable stimulator of claim 1 further characterized in that an off-on indicator light forms part of said pulse generator to provide indication of current flow to said pulse generator.

8. The electrically operable stimulator of claim 1 further characterized in that a rechargeable source of stored electrical energy forms part of said stimulator and is operatively connected to said pulse generator.

* * * * *